(12) United States Patent
Turcott

(10) Patent No.: US 6,997,879 B1
(45) Date of Patent: Feb. 14, 2006

(54) METHODS AND DEVICES FOR REDUCTION OF MOTION-INDUCED NOISE IN OPTICAL VASCULAR PLETHYSMOGRAPHY

(75) Inventor: Robert G. Turcott, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 103 days.

(21) Appl. No.: 10/192,368

(22) Filed: Jul. 9, 2002

(51) Int. Cl.
*A61B 5/02* (2006.01)
*A61B 5/00* (2006.01)

(52) U.S. Cl. .................. 600/507; 600/500; 600/336
(58) Field of Classification Search ............... 600/507, 600/500–504, 481, 485, 476, 477, 479, 480, 600/473, 475, 310–341
See application file for complete search history.

(56) References Cited

U.S. PATENT DOCUMENTS

| | | | |
|---|---|---|---|
| 3,139,086 A | 6/1964 | Botsch et al. | |
| 3,412,729 A | 11/1968 | Smith, Jr. | |
| 4,030,485 A | 6/1977 | Warner | |
| 4,157,708 A | 6/1979 | Imura | |
| 4,266,554 A * | 5/1981 | Hamaguri | 600/323 |
| 4,407,290 A | 10/1983 | Wilber | |
| 4,418,700 A | 12/1983 | Warner | |
| 4,541,439 A * | 9/1985 | Hon | 600/504 |
| 4,621,643 A | 11/1986 | New, Jr. et al. | |
| 4,653,498 A | 3/1987 | New, Jr. et al. | |
| 4,714,080 A * | 12/1987 | Edgar et al. | 600/330 |
| 4,714,341 A | 12/1987 | Hamaguri et al. | |
| 4,730,389 A | 3/1988 | Baudino et al. | |
| 4,750,495 A | 6/1988 | Moore et al. | |
| 4,815,469 A | 3/1989 | Cohen et al. | 128/634 |
| 4,819,752 A | 4/1989 | Zelin | |
| 4,832,484 A | 5/1989 | Aoyagi et al. | |
| 4,834,107 A | 5/1989 | Warner | |
| 4,907,594 A * | 3/1990 | Muz | 600/335 |
| 5,040,533 A | 8/1991 | Fearnot | |
| 5,040,538 A | 8/1991 | Mortazavi | |
| 5,055,671 A * | 10/1991 | Jones | 250/227.21 |
| 5,176,137 A | 1/1993 | Erickson et al. | |

(Continued)

FOREIGN PATENT DOCUMENTS

EP    0 524 083 A1    7/1992

(Continued)

OTHER PUBLICATIONS

Coetzee, et al., "Noise-Resistant Pulse Oximetry Using a Synthetic Reference Signal", IEEE Transactions on Biomedical Engineering, vol. 47, No. 8, Aug. 2000, pp. 1018-1026.

(Continued)

*Primary Examiner*—Robert L. Nasser
*Assistant Examiner*—Navin Natnithithadha
(74) *Attorney, Agent, or Firm*—Steven M. Mitchell

(57) ABSTRACT

Methods and devices are provided for reducing motion artifacts when monitoring volume changes in blood vessels. Light having a first wavelength and light having a second wavelength are transmitted through a human appendage, toward the epidermis of a patient, or through tissue within the body of a patient. A portion of the light having the first wavelength and a portion of the light having the second wavelength is received. A first signal is produced based on the received portion of light having the first wavelength. A second signal is produced based on the received portion of light having the second wavelength. One of the first and second signals is subtracted from the other to produce a plethysmography signal that is representative of volume changes in blood vessels of patient tissue.

10 Claims, 10 Drawing Sheets

U.S. PATENT DOCUMENTS

| | | | |
|---|---|---|---|
| 5,222,495 A | | 6/1993 | Clarke et al. |
| 5,246,002 A | * | 9/1993 | Prosser ................. 600/336 |
| 5,349,961 A | | 9/1994 | Stoddart et al. |
| 5,396,893 A | | 3/1995 | Oberg et al. |
| 5,413,100 A | | 5/1995 | Barthelemy et al. |
| 5,421,329 A | | 6/1995 | Casciani et al. |
| 5,490,505 A | * | 2/1996 | Diab et al. ................. 600/323 |
| 5,499,627 A | | 3/1996 | Steuer et al. |
| 5,544,661 A | | 8/1996 | Davis et al. |
| 5,556,421 A | | 9/1996 | Prutchi et al. |
| 5,676,141 A | | 10/1997 | Hollub |
| 5,730,125 A | * | 3/1998 | Prutchi et al. ............. 600/323 |
| 5,779,631 A | * | 7/1998 | Chance .................. 600/328 |
| 5,857,975 A | | 1/1999 | Golub |
| 5,862,805 A | | 1/1999 | Nitzan |
| 5,865,755 A | | 2/1999 | Golub ................. 600/485 |
| 5,891,022 A | | 4/1999 | Pologe ................. 600/323 |
| 5,954,644 A | | 9/1999 | Dettling et al. ............. 600/322 |
| 6,018,673 A | | 1/2000 | Chin et al. ................. 600/322 |
| 6,064,898 A | * | 5/2000 | Aldrich ................. 600/316 |
| 6,104,938 A | | 8/2000 | Huiku et al. ................. 600/322 |
| 6,122,536 A | | 9/2000 | Sun et al. ................. 600/341 |
| 6,151,516 A | * | 11/2000 | Kiani-Azarbayjany et al. ................. 600/322 |
| 6,374,129 B1 | | 4/2002 | Chin et al. ................. 600/322 |
| 6,393,311 B1 | | 5/2002 | Edgar et al. ................. 600/323 |

FOREIGN PATENT DOCUMENTS

| | | |
|---|---|---|
| WO | WO 94/03102 | 2/1994 |

OTHER PUBLICATIONS

Yoshiya, et al.; "Spectrophotometric Monitoring of Arterial Oxygen Saturation in the Fingertip"; Medical & Biological Engineering & Computing; Jan. 1980; pp 27-32.

Flewelling; "Noninvasive Optical Monitoring"; Biomedical Engineering Handbook; CRC Press, Inc., 1995; pp. 1346-1356.

* cited by examiner

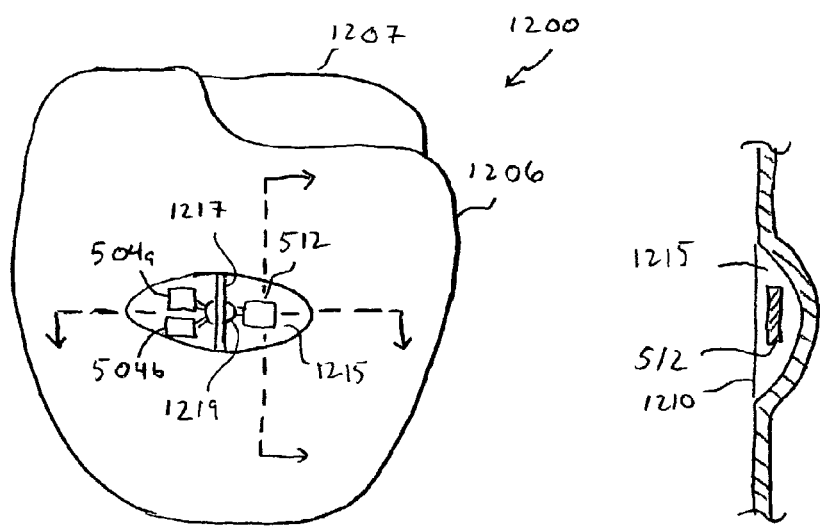
FIG 12a
FIG. 12c
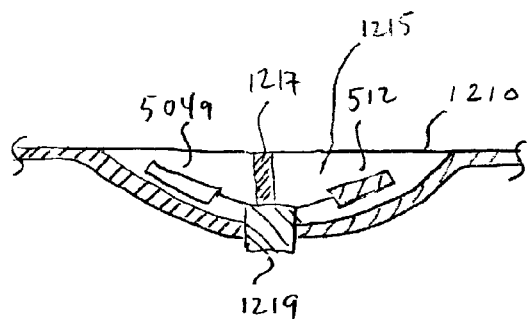
FIG 12b

METHODS AND DEVICES FOR REDUCTION OF MOTION-INDUCED NOISE IN OPTICAL VASCULAR PLETHYSMOGRAPHY

BACKGROUND OF THE INVENTION

1. Field of the Invention

The present invention relates generally to non-invasive and implantable plethysmography methods and devices. The present invention more particularly relates to methods and devices for monitoring volume changes in a limb or tissue segment of a patient.

2. Related Art

Plethysmography is a generic term referring to a variety of techniques for monitoring volume changes, for example, volume changes of the lungs due to respiration, or of blood vessels of a limb or tissue segment. When applied to measurements of blood volume, changes occur in a pulsatile manner with each beat of the heart as blood flows in and out of a portion of the body. The study of vascular activity by fluid displacement methods dates back to at least 1890. More contemporary techniques include strain gauge, pneumatic, impedance, doppler, and photoelectric plethysmography. A plethysmography device produces a waveform that is similar to an arterial pressure waveform. The waveform is useful in measuring pulse velocity and indicating arterial obstructions.

FIG. 1 illustrates an exemplary plethysmograph 100, which includes a waveform 102 produced by a plethysmography device. For timing reference, an electrocardiogram (ECG) signal 104 is illustrated. Waveform 102 provides a measure of the volume of the arterial vasculature. A measure of arterial pulse amplitude is derived from it. A few tens to a few hundreds of milliseconds after the QRS complex, the plethysmography voltage reaches a minimum and starts to increase. This is due to the increasing blood volume in the arterioles as the systolic pulse reaches the periphery. The delay is influenced by the distance that the sensor is placed from the heart. It requires approximately 100 msec for the waveform to reach its maximum. The excursion from minimum to maximum represents the arterial pulse amplitude. During diastole, the recoil of the elastic arterial vessels continues to force blood through the capillaries, so that blood flows through the capillary bed throughout the entire cardiac cycle.

A photoplethysmography device (PPG) (also called a pseudoplethysmography or photoelectric plethysmography device) includes a light detector and a light source. The PPG utilizes the transmission or reflection of light to demonstrate the changes in blood perfusion. Such devices might be used in the cardiology department or intensive care department of a hospital or in a clinic for diagnostic purposes related to vascular surgery. A photoplethysmography device is also referred to, herein, simply as a plethysmography device.

An exemplary circuit 200A for a conventional photoplethysmography device is shown in FIG. 2A. An exemplary mechanical arrangement 200B for a conventional photoplethysmography device is shown in FIG. 2B. In these examples, the light source includes a light-emitting diode (LED) 202, although in alternative models an incandescent lamp can be used. The light detector in this example includes a photoresistor 204 excited by a constant current source. Changes in light intensity cause proportional changes in the resistance of photoresistor 204. Since the current through photoresistor 204 is constant in this example, the resistance changes produce varying analog voltage ($V_{out\_analog}$) at the output terminal. This varying analog voltage ($V_{out\_analog}$) is typically converted to a digital signal ($V_{out\_digital}$) using an analog to digital converter (A/D) 206. Other known light detectors include photo diodes, photo transistors, photo darlingtons and avalanche photo diodes.

Light may be transmitted through a capillary bed such as in an ear lobe or finger tip. As arterial pulsations fill the capillary bed the changes in volume of the blood vessels modify the absorption, reflection and scattering of the light. Stated another way, an arterial pulse in, for example, a finger tip, or ear lobe, causes blood volume to change, thereby changing the optical density of the tissue. Therefore, the arterial pulse modulates the intensity of the light passing through the tissue. Light from LED 202 is reflected into photoresistor 204 by scattering and/or by direct reflection from an underlying bone structure. Such a PPG does not indicate "calibratable" value changes. Thus, its usefulness is generally limited to pulse-velocity measurements, determination of heart rate, and an indication of the existence of a pulse (e.g., in a finger). Additionally, a conventional PPG provides a poor measure of changes in volume and is very sensitive to motion artifacts.

It is noted that photoplethysmography devices may operate in either a transmission configuration or a reflection configuration. In the transmission configuration, LED 202 and the photodetector 204 face one another and a segment of the body (e.g., a finger or earlobe) is interposed between them. In the reflection configuration, LED 202 and photodetector 204 are mounted adjacent to one another, e.g., on the surface of the body, as shown in FIG. 2B.

A problem with optical methods and devices for performing vascular plethysmography is that they are acutely sensitive to sensor and/or tissue motion. Even rather subtle motion can swamp the plethysmography signal and render it unusable. For example, with plethysmography devices that measure blood volume changes in a fingertip or earlobe, such subtle motion may be caused by a patient's slight movement of their finger or head. Accordingly, there is a need to reduce motion-induced noise in optical vascular plethysmography.

SUMMARY OF THE INVENTION

The present invention relates to methods and devices for reducing motion artifacts when monitoring volume changes in blood vessels. Light having a first wavelength and light having a second wavelength are transmitted through a human appendage, toward the epidermis of a patient, or through tissue within the body of a patient. A portion of the light having the first wavelength and a portion of the light having the second wavelength is received. A first signal is produced based on the received portion of light having the first wavelength. A second signal is produced based on the received portion of light having the second wavelength. One of the first and second signals is subtracted from the other to produce a plethysmography signal that is representative of volume changes in blood vessels of patient tissue.

Devices for monitoring volume changes in blood vessels, in accordance with embodiments of the present invention, include a light source, a light detector and a comparator. The light source transmits the light having the first wavelength and the light having the second wavelength through the patient tissue (e.g., in a human appendage). The light detector receives the portion of the light having the first wavelength and the portion of the light having the second wavelength and produces the first signal, based on the received portion of light having the first wavelength, and the second signal, based on the received portion of the light having the second wavelength. The comparator (e.g., a differential amplifier) subtracts one of the first and second signals from the other to produce the plethysmography signal of interest.

The light source can include a first light emitting diode to produce the light having the first wavelength, and a second light emitting diode to produce the light having the second wavelength. Alternatively, lasers or laser-diodes can be used to produce light at specific wavelengths. The light source can alternatively be a broad-spectrum source such as an incandescent lamp or a tungsten halogen lamp. With a broad spectrum source, frequency selective optical filters are used to provide signals corresponding to each wavelength.

The light detector can include a first photodetector (also known as a photocell) to receive the portion of the light having the first wavelength, and a second photodetector to receive the portion of the light having the second wavelength. Alternatively, the same photodetector can detect both the first portion of light having the first wavelength and the second portion of light having the second wavelength. In this case, the light detector may include a demultiplexor to separate a first portion of a voltage signal representative of the first portion of light having the first wavelength from a second portion of the voltage signal representative of the second portion of light having the second wavelength. The light detector can also include a first bandpass filter to produce the first signal from the first portion of the voltage signal, and a second bandpass filter to produce the second signal from the second portion of the voltage signal. Such a photodetector(s) can be, for example, a photodiode, a photo resistor, a photo darlington or a photo transistor.

In non-implantable embodiments, the transmitted light having the first wavelength and the transmitted light having the second wavelength can be transmitted through a patient's finger, earlobe, foot or hand. The light can also be applied to the epidermis of a patient at various other locations about a patient's body. In implantable embodiments of the present invention, the light source and the light detector are incorporated into an implantable housing and the light having a first wavelength and light having a second wavelength are transmitted toward tissue within the patient's body.

In accordance with an embodiment of the present invention, the first wavelength is less than 650 nm (e.g., 600 nm) and the second wavelength is greater than 650 nm (e.g., 805 nm).

In accordance with an embodiment of the present invention, a ratio of an intensity of the light having the first wavelength and an intensity of the light having the second wavelength is adjusted to reduce motion artifacts. Preferably, the ratio is adjusted to minimize the motion artifacts. Alternatively or additionally, a ratio of a gain of the first signal and a gain of the second signal is adjusted to reduce (and preferably minimize) the motion artifacts.

In accordance with an embodiment of the present invention, the intensities are set such that a ratio of an intensity of the light having the first wavelength over an intensity of the light having the second wavelength is approximately equal to a ratio of an effective absorption coefficient of non-blood tissue at the second wavelength over an effective absorption coefficient of non-blood tissue at the first wavelength.

Further features and advantages of the present invention may be more readily understood by reference to the following description taken in conjunction with the accompanying drawings and claims.

BRIEF DESCRIPTION OF THE DRAWINGS/FIGURES

The left-most digit(s) of a reference number identifies the drawing in which the reference number first appears.

FIG. 12 illustrates an implantable device, according to an embodiment of the present invention.

DETAILED DESCRIPTION OF THE INVENTION

Figure 1:
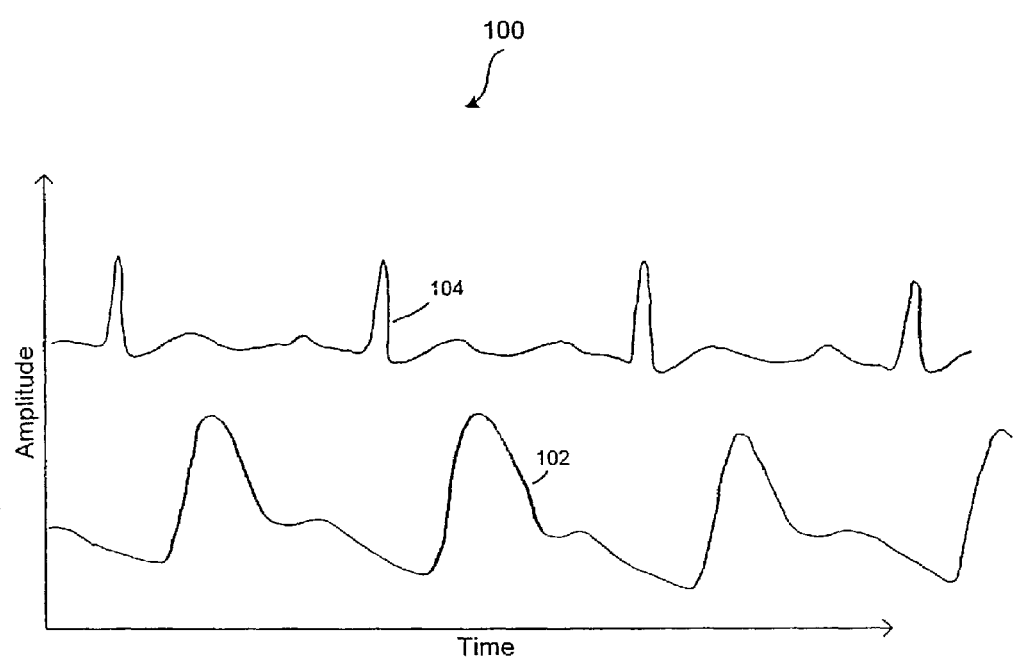
FIG. 1 illustrates an exemplary waveform produced by a plethysmography device.

The following description is of the best modes presently contemplated for practicing the invention. This description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout.

In accordance with an embodiment of the present invention, the requirements on the optical properties of a photoplethysmography system which minimizes noise artifact are defined mathematically using a modified version of the Beer-Lambert law. The Beer-Lambert law relates attenuation of light intensity to the optical pathlength and optical properties of a sample. The absorption coefficients that appear in the Beer-Lambert law are defined under precisely controlled laboratory conditions. In a practical setting, particularly with living biological tissues, the measured absorption of the material may deviate from what is measured in the laboratory. This can occur for a number of reasons, including the effect of scattering on the light path, the geometrical orientation of the light source and detector, and anisotropic nature of the tissue. Furthermore, there are many distinct substances in tissue, each with their own absorption properties. Embodiments of the present invention account for these deviations from the model and incorporate the effect of multiple absorbing constituents by using effective absorption coefficients and effective pathlengths. Furthermore, precise knowledge of the values of effective absorption coefficients and effective pathlengths is not necessary for the function of the invention.

In the modified version of the Beer-Lambert law, let $K_t$ and $K_b$ be the effective absorption coefficients of the non-blood tissue and the blood, respectively, and let $l_t(t)$ and $l_b(t)$ be the effective time-varying optical pathlength of each. In general, motion will influence the effective optical path length of the blood. However, for small perturbations, the change in interstitial pressure due to motion is small relative to the blood pressure, so the effect of motion on the optical pathlength of the blood can be neglected. Thus, the effect of motion is contained in the optical pathlength of the non-blood tissue, $l_t(t)$, while the time-varying vascular volume is contained in the optical pathlength of the blood, $l_b(t)$. The modified version of the Beer-Lambert law predicts that the detected light intensity, $I$, is related to the effective incident light intensity, $I_0$, by $$I = I_0 \exp(-K_t l_t(t) - K_b l_b(t)).$$

In this adaptation of the Beer-Lambert law, the effective incident light intensity $I_0$ is not the same as the total light intensity generated at the source, most of which is scattered away by the tissue. Rather, it is that fraction of the total intensity that would impinge on the detector had it not been absorbed by the non-blood tissue or blood.

Using subscripts to indicate the intensities and absorption coefficients of two different wavelengths of light, $\lambda_1$ and $\lambda_2$, and taking the difference between the detected signals, we have $$I_1 - I_2 = I_{0,1} \exp(-K_{t1} l_t(t) - K_{b1} l_b(t)) - I_{0,2} \exp(-K_{t2} l_t(t) - K_{b2} l_b(t))$$

Since the products of the absorption coefficients and the optical pathlengths are small compared to unity, we can use the approximation $e^{-x} \cong 1-x$, so that $$I_1 - I_2 = I_{0,1} - I_{0,2} + l_t(t)(-I_{0,1} K_{t1} + I_{0,2} K_{t2}) + l_b(t)(-I_{0,1} K_{b1} + I_{0,2} K_{b2})$$

$$= I_{0,1} - I_{0,2} + l_t(t)(I_{0,1} K_{t1})\left(\frac{I_{0,2} K_{t2}}{I_{0,1} K_{t1}} - 1\right) + l_b(t)(I_{0,1} K_{b1})\left(\frac{I_{0,2} K_{b2}}{I_{0,1} K_{b1}} - 1\right)$$

$$= I_{0,1} - I_{0,2} + l_t(t)(I_{0,1} K_{t1})\left[\left(\frac{I_{0,2}}{I_{0,1}}\right)\left(\frac{K_{t2}}{K_{t1}}\right) - 1\right] + l_b(t)(I_{0,1} K_{b1})\left[\left(\frac{I_{0,2}}{I_{0,1}}\right)\left(\frac{K_{b2}}{K_{b1}}\right) - 1\right]$$

If the intensity of the sources is set so that $r_{opt} = I_{0,2}/I_{0,1} = K_{t1}/K_{t2}$, then the multiplier of $l_t(t)$ becomes zero and the effect of motion is removed from the difference signal. Furthermore, if wavelengths $\lambda_0$ and $\lambda_2$ are chosen such that the ratios of absorption coefficients of tissue and blood are not equal, i.e., $K_{t2}/K_{b2} \neq K_{t1}/K_{b1}$, then the multiplier of the blood pathlength is not zero, and the plethysmography signal is preserved. Under these constraints, the difference signal becomes $$I_1 - I_2 = I_{0,1} - I_{0,2} + l_b(t)(I_{0,1} K_{t1})\left[\left(\frac{I_{0,2}}{I_{0,1}}\right)\left(\frac{K_{b2}}{K_{b1}}\right) - 1\right],$$

which depends entirely on the optical pathlength of the blood, and not on the optical pathlength of the tissue. Thus, the effect of motion on the tissue is removed from the detected signal.

Figure 4A:
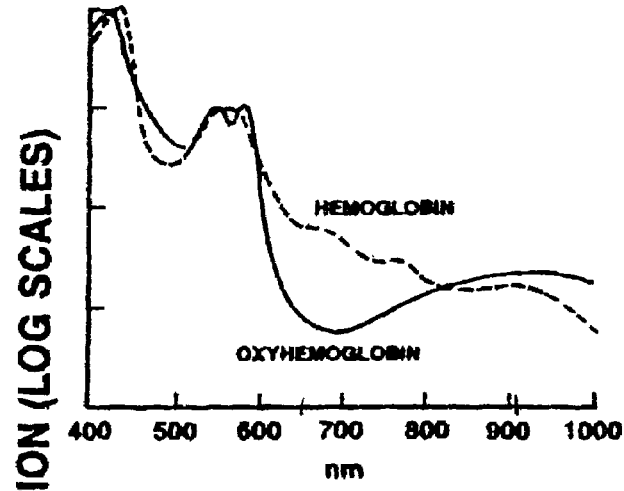
FIGS. 4A–4D shows graphs of absorption spectrum for various blood and non-tissue elements.
Figure 4B:
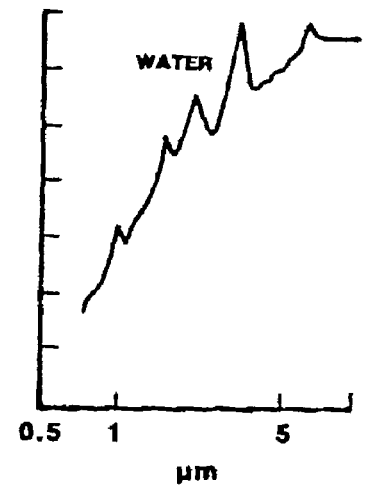
Figure 4C:
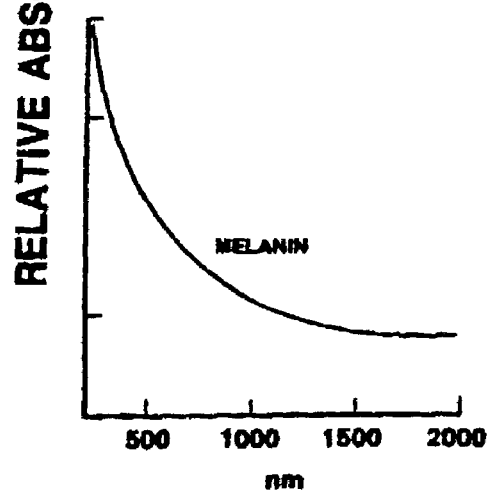

The hemoglobin component of blood strongly absorbs light with wavelengths below around 600 nm, while water is strongly absorbing above around 900 nm. In the range 600–900 nm there is an isobestic point near 805 nm where the absorption of oxygenated hemoglobin (also referred to as oxyhemoglobin) is precisely equal to that of deoxygenated hemoglobin (also simply referred to as hemoglobin). This is shown in a absorption versus wavelength graph shown in FIG. 4A. Setting one wavelength to 805 nm is desirable because it makes the performance of the plethysmograph insensitive to changes in oxygen saturation. In applications such as pulse oximetry, where the photoplethysmograph is used to detect changes in blood oxygen saturation, the isobestic point is not necessarily a desirable wavelength to use.

Figure 4D:
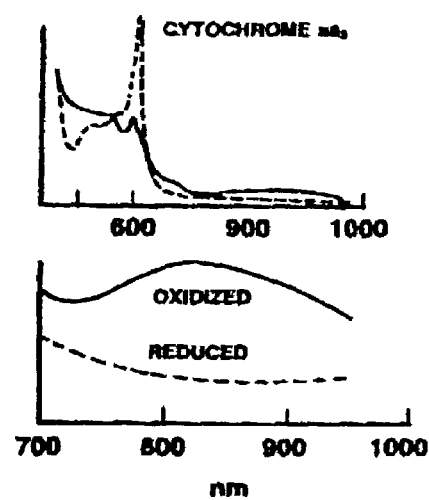

For any two wavelengths that satisfy $K_{t2}/K_{b2} \neq K_{t1}/K_{b1}$, the source intensities $I_{0,1}$ and $I_{0,2}$ can be adjusted to minimize the motion signal while preserving the plethysmography signal. In order to maximize the preserved plethysmography signal, however, the wavelengths should be judiciously chosen so that the difference between $r_1 = K_{t1}/K_{b1}$ and $r_2 = K_{t2}/K_{b2}$ is relatively large. With $\lambda_1$ set near 805 nm (for the reasons described above) this can be achieved by setting $\lambda_2$ near 600 nm, which is the location of a strong absorption peak in another major absorber of light in tissue, cytochrome aa3. This is shown in a absorption versus wavelength graph shown in FIG. 4D.

Like all models of physical and biological systems, the modified Beer-Lambert relation law of the present invention is an approximation. Some deviation from the mathematical prediction is expected, particularly as scattering plays an important role in biological applications. Despite this, the general result will remain true, that is, a ratio of relative intensities $I_{0,2}/I_{0,1}$ can be chosen which preferentially minimizes the effect of motion on the detected signal, while preserving the effect of changing vascular volume.

Because of the potential for deviation from the model, as well as for convenience, it may be desirable to empirically determine the optimal ratio $r_{opt} = I_{0,2}/I_{0,1}$ rather than base it on published values of $K_t$ and $K_b$ and theoretical modeling. This can be done by adjusting the average intensity of one of the sources while applying a controlled mechanical motion to the tissue. In this case, $r_{opt}$ will be taken as the ratio of incident intensities which empirically minimizes the effect of motion in the detected signal.

LEDs are attractive light sources because they produce a narrow range of wavelengths around the nominal value. Furthermore, their operation and the associated control circuitry is simple. Laser diodes and lasers are other possible narrow-spectrum sources. Broad spectrum sources can also be used, with optical filtering performed at the source or detector to provide two effective wavelengths.

Figure 3:
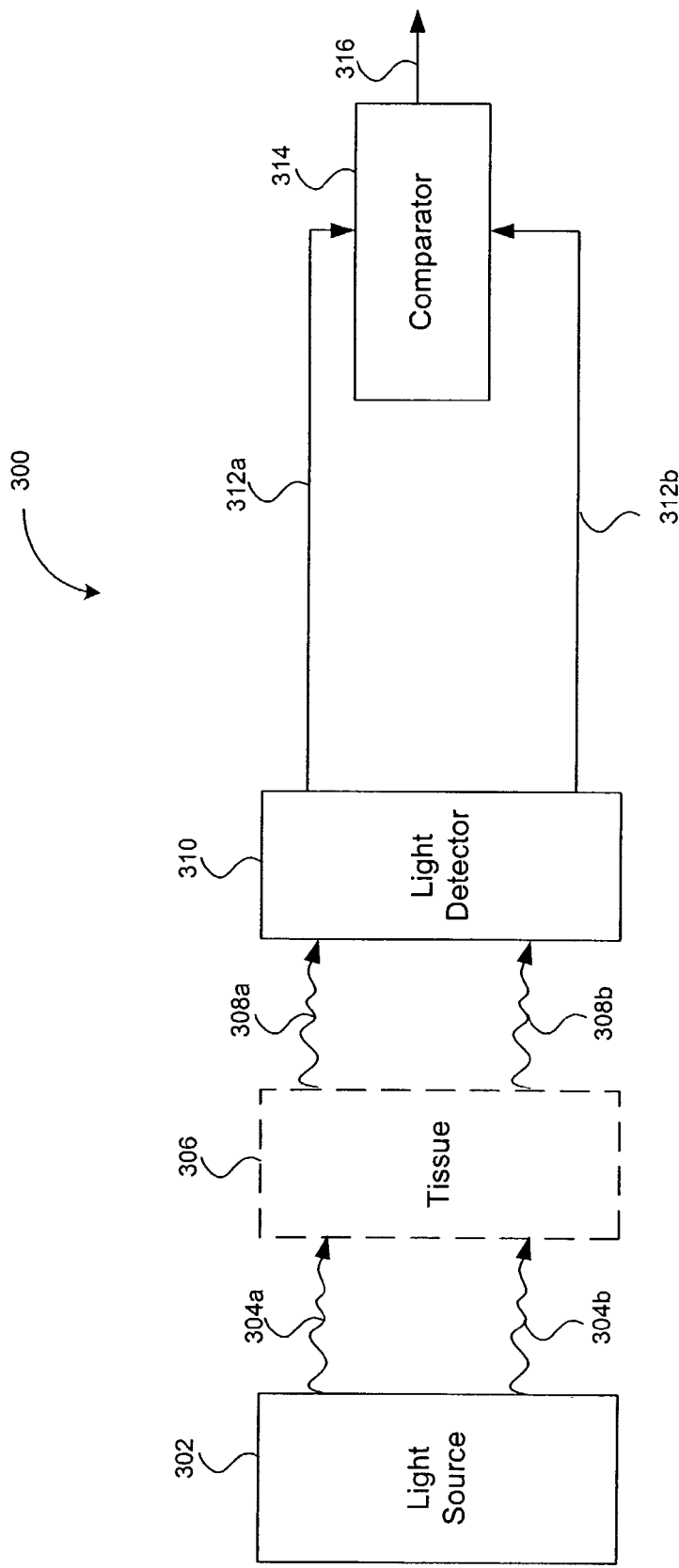
FIG. 3, is a block diagram that illustrates an overview of a photoplethysmography device according to an embodiment of the present invention.

FIG. 3 includes a high level block diagram 300 that provides an overview of the present invention. A light source 302 produces a first transmit light signal 304a and a second transmit light signal 304b. First transmit light signal 304a has a first wavelength $\lambda_1$ that is strongly absorbed by blood, such as near 550 nm or near 600 nm. Second transmit light signal 304b has a wavelength $\lambda_2$ that is absorbed more weakly by blood, such as near 905 nm or near 805 nm. Light signals 304a and 304b are transmitted through and/or reflected by (depending on the embodiment) patient tissue 310, which includes non-blood tissue and blood (i.e., red blood cells). As light signals 304a and 304b travel through patient tissue 310, some of the light energy of each signal is absorbed by blood and some of the light is absorbed by non-blood tissue. However, due to the selected wavelengths, much more energy of first light signal 304a is absorbed by the blood than energy of second light signal 304b. In contrast, the energy of first light signal 304a absorbed by the non-blood tissue and the energy of second light signal 304b absorbed by the non-blood tissue are similar.

The intensity of a transmitted light signals 304a and 304b can be changed by changing the amplitude of the driving current, or for pulsed configurations, the pulse width, frequency, or duty cycle of the current.

A first receive light signal 308a (having the first wavelength $\lambda_1$) and a second receive light signal 308b (having the second wavelength $\lambda_2$) are received at a light detector 310. Light detector 310 outputs a first signal 312a and a second signal 312b. First signal 312a (associated with the first wavelength $\lambda_1$) and second signal 312b (associated with the second wavelength $\lambda_2$) are both representative of volume changes in the non-blood tissue and in blood, with volume changes in the non-blood tissue being primarily due to motion. Since the effective absorption ratios $r_1$ (associated the first wavelength $\lambda_1$) and $r_2$ (associated with the second wavelength $\lambda_2$) are different (as discussed above), the amplitudes of first signal 312a and second signal 312b are different. It is this difference between the two signals 312a and 312b that contains the plethysmography information of interest.

First signal 312a and second signal 312b are compared by a comparator 314. The term "comparator" is used herein to refer to a device (or possibly software) that performs a comparison between two input signals and generates an output based on the results of the comparison. Comparator 314 outputs a difference signal 316 which is equal to second signal 312b subtracted from first signal 312a (or vice versa). Difference signal 316 is a plethysmography signal representative of volume changes in the blood vessels of the patient tissue with motion artifacts reduced and preferably substantially removed or minimized.

Figure 5:
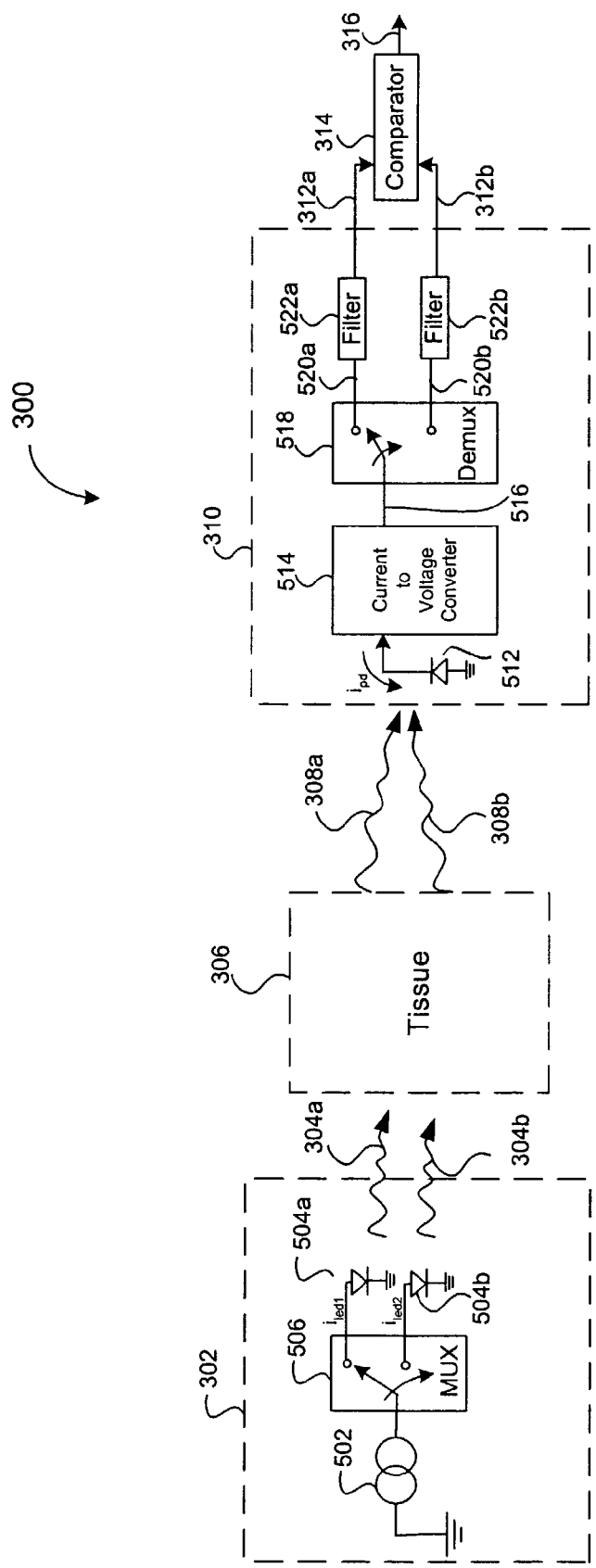
FIG. 5 is a block diagram that illustrates an implementation of the plethysmography device of FIG. 3, according to an embodiment of the present invention.
Figure 9:
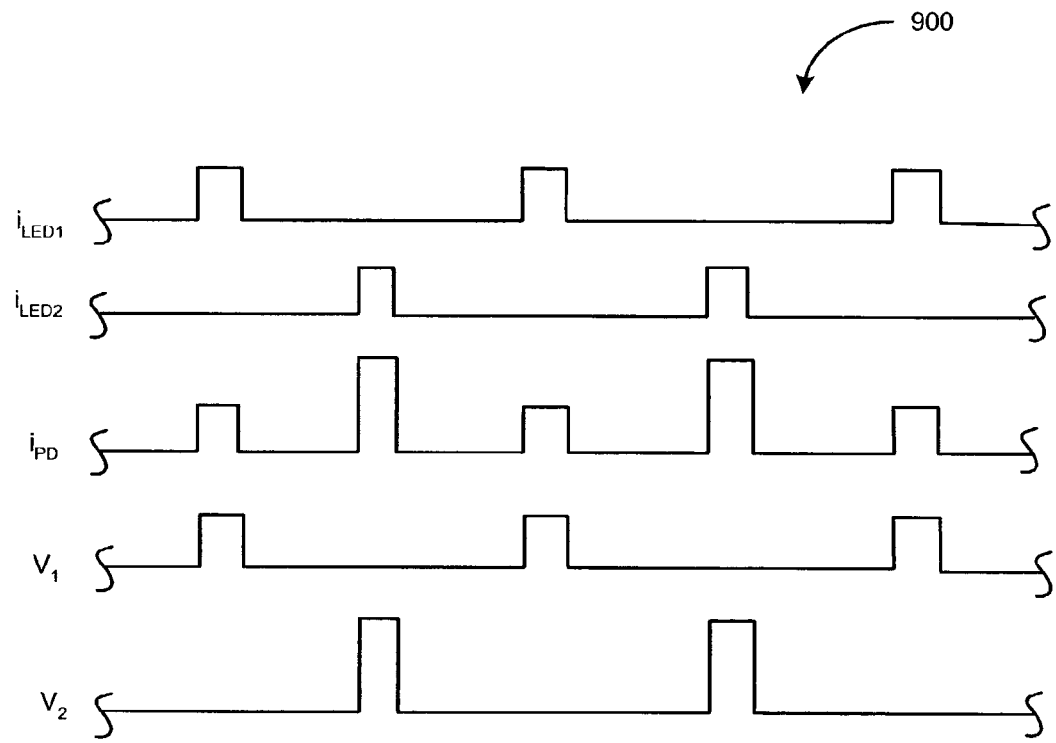
FIG. 9 is a timing diagram that is useful for explaining the operation of the embodiment of FIG. 5.

Additional details of the elements of block diagram 300, according to an embodiment of the present invention, are described with reference to FIG. 5. Referring now to FIG. 5, in accordance with an embodiment of the present invention, light source 302 includes a current source 502, a first LED 504a and a second LED 504b. First LED 504a produces light having a first wavelength below 650 nm (e.g., 600 nm) and second LED 504b produces light having a wavelength above 650 nm (e.g., 805 nm). A multiplexor 506 provides a current signal $i_{LED}$, produced by current source 502, to one of first LED 504a and second LED 504b, in a time multiplexed manner. This produces a first light control signal $i_{LED1}$ that drives first LED 504a and a second light control signal $i_{LED2}$ that drives second LED 504b. FIG. 9 illustrates a timing diagram 900 that is useful for explaining the relationship between first light control signal $i_{LED1}$ and second light control signal $i_{LED2}$. As shown in timing diagram 900, first light control signal $i_{LED1}$ and second light control signal $i_{LED2}$ preferably include non-overlapping pulses. As would be appreciated by one of ordinary skill in the art, two separate pulse generates can be used in place of current source 502 and multiplexor 506.

In accordance with an embodiment of the present invention, light detector 310 includes a photodetector 512 operated in a current sensing photoconductive mode. Photodetector 512 (e.g., a photodiode), produces a photodetector current signal $i_{pd}$ that is fed to a current to voltage converter 514. Current-to-voltage converted 514 converts a photodiode current ($i_{pd}$) to a voltage signal 516. Voltage signal 516 is provided to a demultiplexor 518, which passes voltage signal 516 to a first path 520a or a second path 520b. Demultiplexor 518 operates synchronously with multiplexor 506 so that portions of voltage signal 516 corresponding to first receive light signal 308a (having the first wavelength $\lambda_1$) are passed to first path 520a, and portions of voltage signal 516 corresponding to second receive light signal 308b (having the second wavelength $\lambda_2$) are passed to second path 520b. The portions of voltage signal 516 provided to first path 520a are also referred to, herein, as first voltage signal 520a. The portions of voltage signal 516 provided to second path 520b are also referred to, herein, as second voltage signal 520b.

Referring again to timing diagram 900, in FIG. 9, the relationship is shown between first light control signal $i_{LED1}$, second light control signal $i_{LED2}$, photodiode current signal $i_{pd}$, first voltage signal 520a and second voltage signal 520b. Assume that pulses in first light control signal $i_{LED1}$ and second light control signal $i_{LED2}$ have the same amplitude, as shown in FIG. 9 (which may not always be the case). Notice that amplitudes of pulses (i.e., samples) associated with second voltage signal 520b are greater than pulses associated with first voltage signal 520a, for the time window shown in FIG. 9. This means that more of first transmit light signal 304a (having the first wavelength $\lambda_1$) than second transmit light signal 304b (having the second wavelength $\lambda_2$) was absorbed (by non-blood tissue and blood of patient tissue 306), during this time window.

Referring back to FIG. 5, first voltage signal 520a is provided to a first filter 522a. Similarly, second voltage signal 520b is provided to a second filter 522b. First filter 522a converts the series of pulses of first voltage signal 520a into a continuous waveform, which is first signal 312a. Similarly, second filter 522b converts the series of pulse of second voltage signal 520b into a continuous waveform, which is second signal 312b. Filters 522a and 522b can also perform band pass filtering to filter out noise that is outside the frequency range of interest. In accordance with an embodiment of the present invention, the frequency range of interest is from about 1 Hz to 10 Hz. The noise removed by filters 522a and 522b can include, for example, 60 Hz noise due to power lines and 120 Hz noise due to fluorescent lights. Filters 522a and 522b can also be used to removes motion artifacts that are outside the frequency range of interest. It is the features of the present invention that remove or reduce the motion artifacts that are within the frequency range of interest.

First signal 312a and second signal 312b are provided to comparator 314. As explained above, comparator 314 outputs plethysmography signal 316. Addition details of comparator 314, according to an embodiment of the present invention, are discussed below with reference to FIG. 8.

Additional details of the elements shown in FIG. 5, according to specific embodiments of the present invention, are now described with reference to FIGS. 6, 7 and 8.

Figure 6:
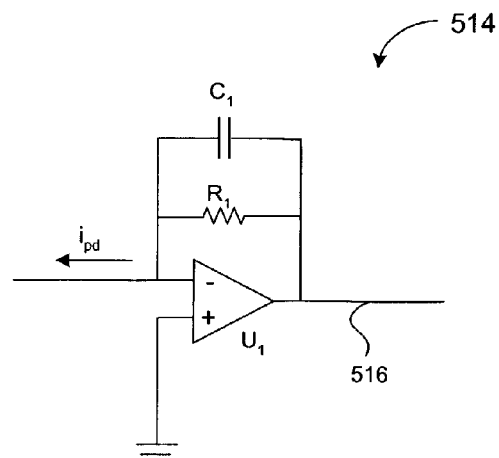
FIG. 6 is a circuit diagram for the current-to-voltage converter of FIG. 5, according to an embodiment of the present invention.

FIG. 6 illustrates a circuit diagram of current-to-voltage converter 514, according to an embodiment of the present invention. In this embodiment, current-to-voltage converter 514 is a transimpedance amplifier that includes a resistor R1, a capacitor C1 and an operational amplifier U1. The transimpedance amplifier performs low pass filtering, anti-alias filtering, and provides gain. The transimpedance amplifier also performs impedance matching that may be necessary where the amplitude of photodiode current signal $i_{pd}$ is not sufficient to drive further components. One of ordinary skill in the art will appreciate that a photodiode can alternatively be operated in a voltage sensing configuration.

One of ordinary skill in the art will appreciate that photodetector 512 can be a photodiode (e.g., an avalanche photodiode), a photo resistor, a photo darlington, a photo transistor, or some other similar detection device, which are all within the spirit and scope of the present invention. One of ordinary skill in the art will also appreciate that other amplifier configurations (e.g., an integrator amplifier, a transistor based amplifier) can be used in place of the transimpedance amplifier shown in FIG. 6. An integrated photodiode/amplifier (e.g., a Burr-Brown OPT101) can also be used. One of ordinary skill in the art will further appreciate that other types of LEDs, or other optical sources, such as, but not limited to laser diodes, lasers and other narrow-spectrum sources can be used to generate the light having the first wavelength and the light having the second wavelength. Broad spectrum sources such as incandescent lamps or tungsten halogen lamps can also be used, with optical filtering performed at the source or detector to provide two effective wavelengths.

Figure 7:
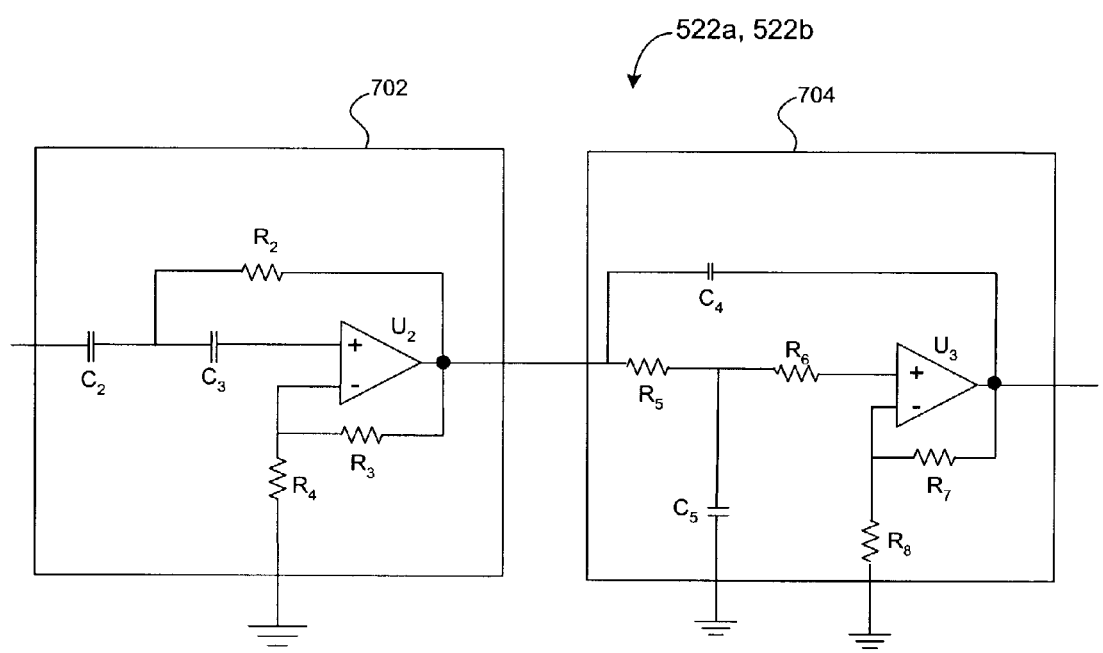
FIG. 7 is a circuit diagram for the filters of FIG. 5, according to an embodiment of the present invention.

FIG. 7 illustrates a circuit diagram that can be used to implement each of filters 522a and 522b, according to an embodiment of the present invention. In this embodiment, filter 522 includes a high pass filter 702 followed by a low pass filter 704, which together form a band pass filter. As shown, low pass filter 702 includes capacitors C2 and C3, resistors R2, R3 and R4, and an operational amplifier U2. High pass filter 704 includes capacitors C4 and C5, resistors R5, R6, R7 and R8, and an operational amplifier U3, as shown. The ratio of R3 to R4 and/or the ratio of R7 to R8 can be adjusted to adjust the effective gain of filter 522. One of ordinary skill in the art will appreciate that use of alternative band pass filters are within the spirit and scope of the present invention.

Figure 8:
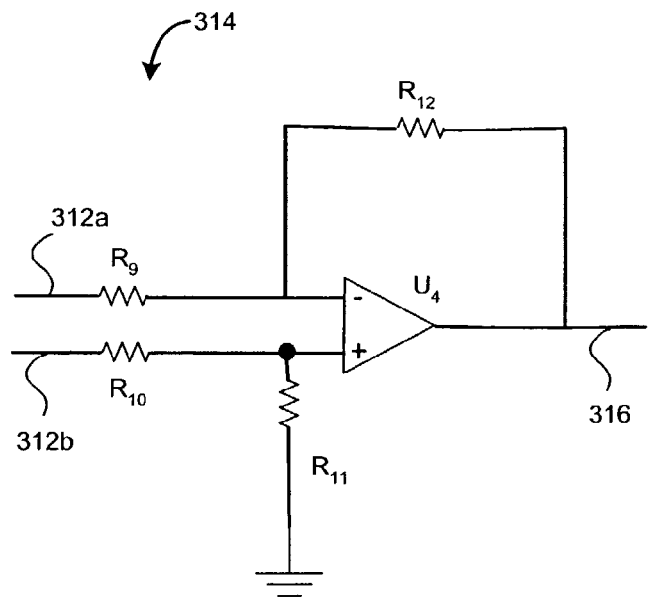
FIG. 8 is a circuit diagram for the comparator of FIG. 5, according to an embodiment of the present invention.

FIG. 8 illustrates a circuit diagram that can be used to implement comparator 314, according to an embodiment of the present invention. In this embodiment, comparator 314 is a differential amplifier that includes resistors R9, R10, R11 and R12, and an operation amplifier U4. The ratio of resistor R11 and R10 can be adjusted to adjust the gain of second signal 312b, and thereby adjust the ratio of first signal 312a to second signal 312b.

Figure 10:
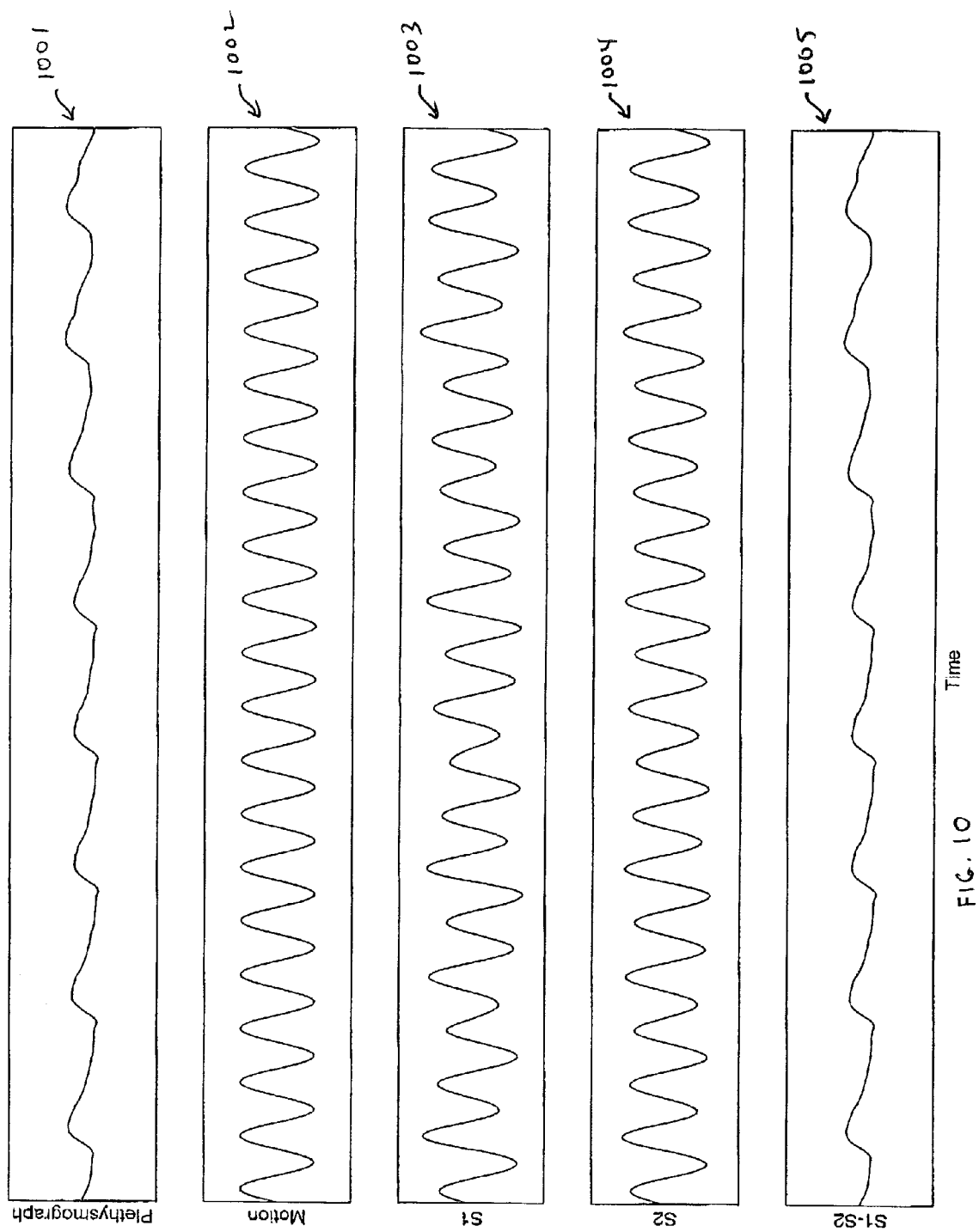
FIG. 10 illustrates exemplary waveforms generated using embodiments of the present invention.

Referring now to FIG. 10, a first waveform 1001 is an exemplary plethysmography signal. Assuming there were no motion artifacts in the non-blood tissue of patient tissue 306, then each of first signal 312a and second signal 312b would resemble this waveform (however, the amplitudes of signal 312a and 312b would be different). Assume that the pulse frequency of this signal is 1.5 Hz, which corresponds to a pulse rate of 90 beats per second. A second waveform 1002 represents exemplary motion artifacts of patient tissue 306. Assume that the frequency of this motion signal is approximately 3.75 Hz. (Of course actual motion artifacts caused by a patient moving and/or breathing would typically have more than one frequency and would have varying amplitude.) A third waveform 1003 represents first signal 312a, which includes both plethysmography information and motion artifacts (due to signal 1002). A fourth waveform 1004 represents second signal 312b, which also includes both plethysmography information and motion artifacts. A fifth waveform 1005, which is a difference between the third waveform 1004 and the fourth waveform 1004, represents desired plethysmography signal 316. Since ratios $r_1 \neq r_2$, the plethysmograhy waveform 1001 and the motion artifact 1002 are combined in different proportions in the first and second signals 312a, 312b. This allows the plethysmography signal to be recovered when their difference (e.g., first signal 312a—second signal 312b) is taken, while the motion artifact is cancelled.

As explained above, the ratio of $I_{0,2}/I_{0,1}$ (which is the ratio of the intensity of first transmit signal 304a to the intensity of second transmit signal 304b) can be adjusted to minimize the effects of a motion signal (e.g., the effects of signal 1002). This is explained below with reference to FIG. 11. Referring briefly back to FIG. 5, the intensity of first transmit light signal 304a or the intensity of second transmit light signal 304b is can be controlled by adjusting, respectively, the amplitude of $i_{LED1}$ or the amplitude of $i_{LED2}$ (e.g., using a potentiometer). If pulses are being used to drive LEDs 504a and 504b (e.g., as shown in FIG. 9), then average intensities can be controlled by adjusting the amplitude and/or the pulse widths of the pulses. That is, increases in pulse width and/or amplitude increases intensity. Since the desire is to adjust the ratio of intensities, an intensity of one of the transmit light signals 304a, 304b can be kept constant while the other one is adjusted. For example, the intensity of first transmit light signal 304a (i.e., $I_{0,1}$) is kept constant, while the intensity of second transmit light signal 304b (i.e., $I_{0,2}$) is adjusted. The desire is to adjust the intensity ratio until motion artifacts are minimized.

Figure 11:
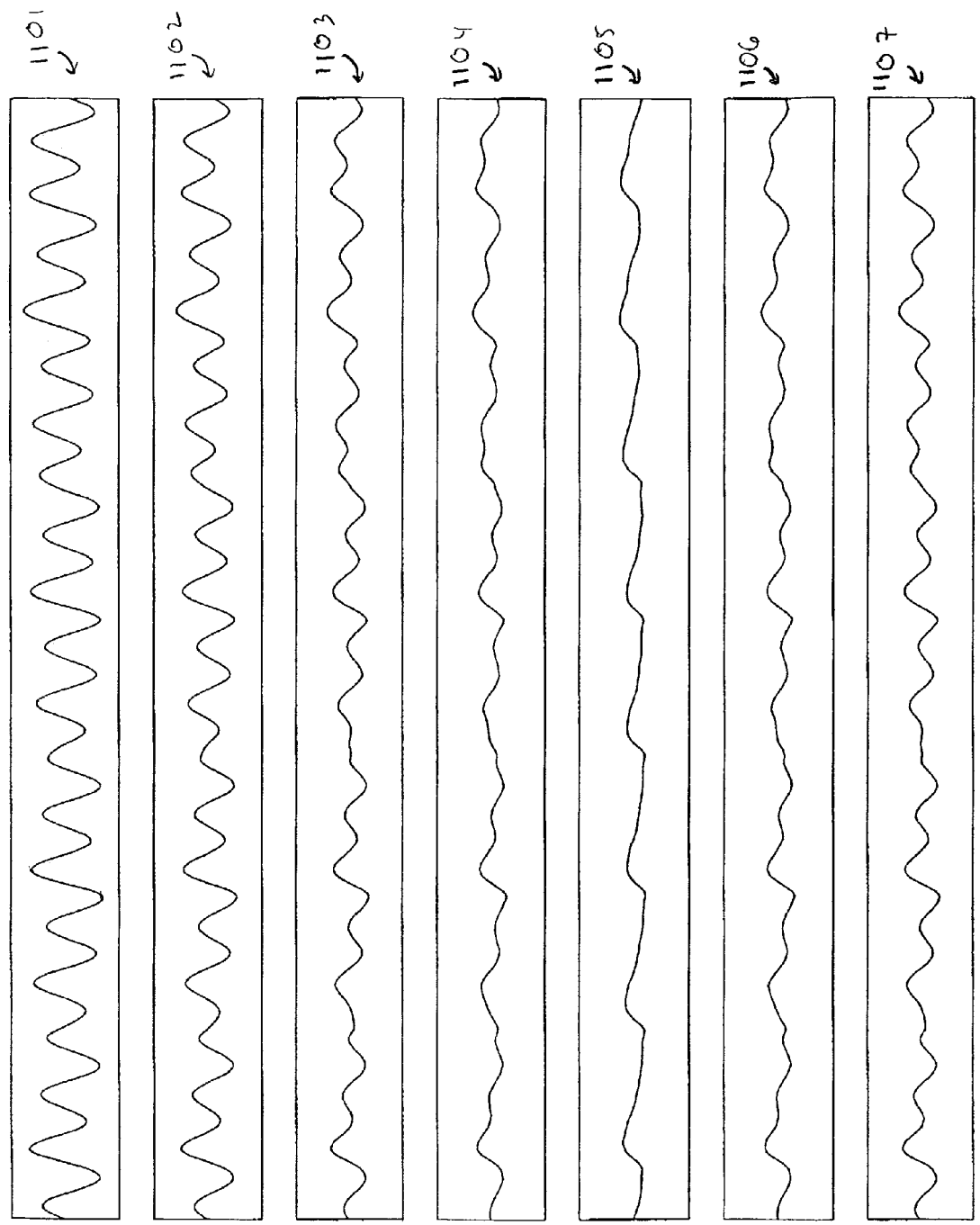
FIG. 11 illustrates various waveforms that are useful for describing how intensity ratios or gain ratios can be adjusted to minimize motion artifacts in accordance with embodiments of the present invention.

Referring now to FIG. 11, each of waveforms 1101–1107 are exemplary plethysmography waveforms 316 (output from comparator 314) with different intensity ratios. As can be observed, the motion artifacts are minimal in waveform 1105. Thus, the intensity ratio that produced this waveform is the preferred ratio. The preferred or substantially optimal ratio can be determined by observing plethysmography signal 316 (e.g., using an appropriate oscilloscope). Alternatively or additionally, a frequency spectral analysis can be performed on plethysmography signal 316. In another embodiment, the variance of plethysmography signal 316 is analyzed and one of the intensities is adjusted (i.e., the ratio is adjusted) until the variance of signal 316 is substantially minimized. Alternatively, the ratio is adjusted until there are a minimum amount of peaks and valleys over a predetermined period of time. These are just a few examples of how the optimal or near optimal intensity ratio can be empirically selected. The optimal ratio can alternatively be theoretically selected using the modified Beer-Lambert law discussed above.

Instead of adjusting the intensity ratio of transmit light signals 304a and 304b, it is equivalent to adjust the gain ratio of signals 312a and 312b. For example, referring to FIGS. 5 and 6, the gain of one of filters 522a and 522b can be adjusted. Alternatively, referring to FIG. 8 (which is an exemplary embodiment of comparator 314), the gain ratio can be adjusted, for example, by adjusting one of resistors R10 or R11.

The above discussed ratios can be adjusted in each plethysmography device such that motion artifacts are minimized for a particular patient. When doing this, a vibrating device (e.g., producing a sinusoidal motion, similar to waveform 1002) can be held against the skin of a patient near the plethysmography device (which may be non-implantable or implantable, as discussed below). Alternatively, and more practical, the ratios are preselected and set such that motion artifacts are minimized for a majority of patients.

Non-Implantable Embodiments

Figure 2A:
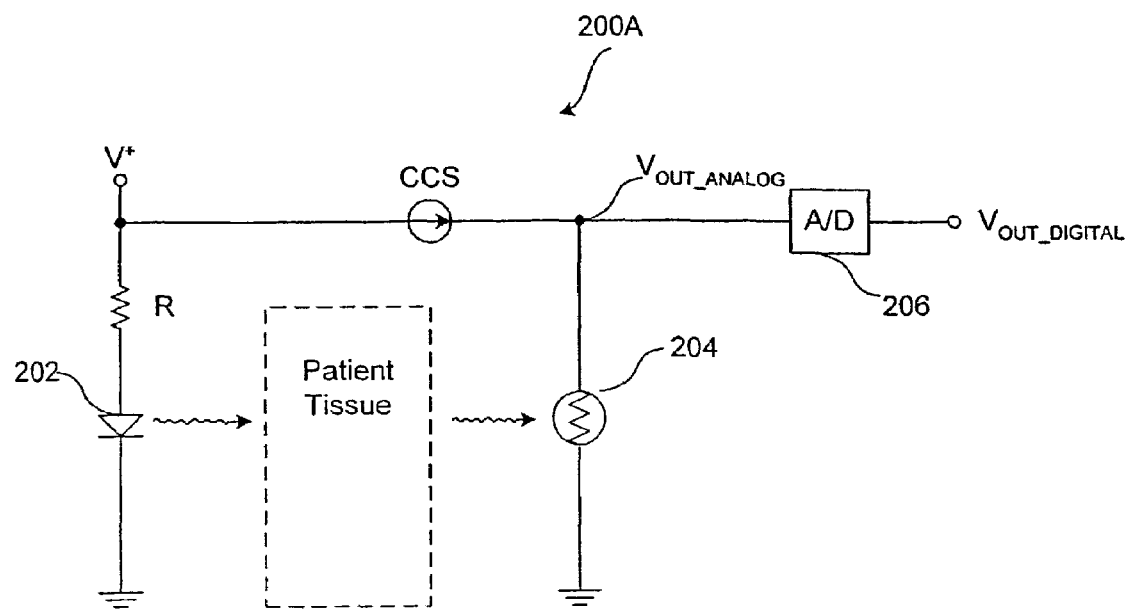
FIG. 2A is a simplified circuit diagram illustrating an exemplary conventional photoplethysmography device.
Figure 2B:
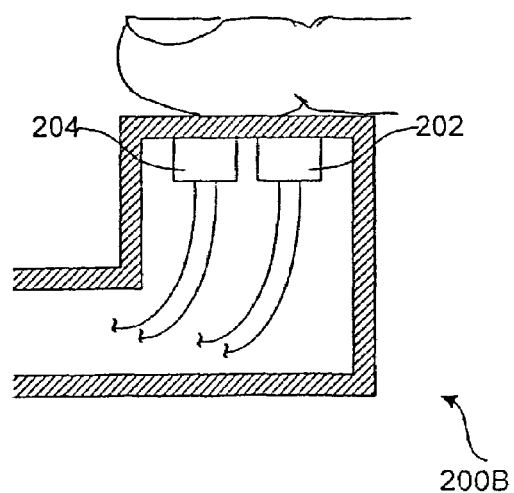
FIG. 2B is a simplified mechanical diagram illustrating a portion of an exemplary conventional photoplethysmography device.

Features of the present invention can be implemented into a non-implantable (i.e., external) device, similar to the one shown in FIG. 2B. The non-implantable devices of the present invention can operate in a transmission or reflection configuration. For example, in a transmission configuration LEDs 504a and 504b would face photodetector 512 so that a human appendage (e.g., a finger, earlobe, hand or foot) can be interposed between the LEDs and detector. In a reflection configuration, LEDs 504a, 504b and photodetector 512 are mounted adjacent to one another and placed against an appendage or against the surface of a patient's body (e.g., against the epidermis of a patient). Accordingly, the phrase "transmitting light through" something (e.g., a human appendage), as used herein, can refer to either a transmission configuration or a reflection configuration.

Implantable Embodiments

Features of the present invention can be incorporated into an implantable device, such as but not limited to an implantable cardioverter defibrillator (ICD) or pacemaker. Alternatively, the features of the present invention can be incorporated into a non-stimulation implantable device whose main purpose is to monitor hemodynamic function. As mentioned above, a problem with optical methods and devices for performing vascular plethysmography is that they are acutely sensitive to sensor and/or tissue motion. With implantable plethysmography devices, such subtle motion may be caused by a patient's walking, or simply breathing. Features of the present invention reduce and preferably minimize the effect of such motion-induced noise.

Exemplary implantable devices of the present invention shall now be described with reference to FIGS. 12A–12C. FIG. 12A shows an implantable device 1200 for monitoring volume changes in blood vessels. As shown, LEDs 504a, 504b and photodetector 512 are incorporated into the housing 1206 of implantable device 1200 (e.g., an ICD, pacemaker, or implantable monitor). LEDs 504a, 504b and photodetector 512 are positioned for a reflected-light configuration. They are preferably placed on the side of device 1200 that, following implantation, faces the interior of the body rather than the surface, and are configured such that light cannot pass directly from LEDs 504a or 504b to photodetector 512. The placement on the side of the device that faces the interior of the body maximizes the signal to noise ratio by 1) directing the signal toward the highly vascularized musculature and 2) shielding the source and detector from ambient light that might enter the body through the skin. In an embodiment, LEDs 504a and 504b and photodetector 512 are placed in a single recess 1215 that is created when the monitor housing 1206 is formed, or, alternatively, machined or cast. An opaque optical barrier 1217 is place between LEDs 504a, 504b and photodetector 512, which ensures that no light passes between them without first interacting with the overlying tissue. Optical barrier 1217 can be made of the same material as device housing 1206, such as titanium or other metal, or can be made from another opaque material such as a polymer. LEDs 504a, 504b and photodetector 512 are physically positioned within recess 1215 such that the amount of reflected light received at photodetector 512 is preferably maximized. In particular, as illustrated in the partial cross section of FIG. 12B, they are angled toward each other with the direction of greatest optical power and sensitivity aligned after reflection from the overlying tissue.

Furthermore, in the preferred embodiment the optical devices have inherent directionality to avoid the need for lenses or other focusing elements, though these are used in alternate embodiments. As illustrated in the cross sections of FIGS. 12B and 12C, recess 1215 has a rounded, concave shape to provide further focusing of stray light. The rounded shape has the added advantage of avoiding low-radius angles which would localize stress when housing 1206 is formed during manufacture. The remaining space in the recess is filled with an epoxy 1210 such that the surface of device 1200 is smooth and flat, thereby minimizing the risk of tissue trauma and infection. The epoxy is preferably of optical quality and transparent at the wavelength of light produced by LEDs 504a, 504b. LEDs 504a, 504b and photodetector 512 are connected via a single feed-through connection 1219 which is hermetically welded to device housing 1206 and connected to the electronic circuit(s) contained within the device 1200. Placing the optical components 502a, 502b and 512 in recess 1215 thereby enhances optical isolation while maintaining hermeticity.

Alternative configurations for the placement of the optical elements (including LEDs 504a, 504b and photodetector 512) can be appreciated from the various embodiments disclosed in U.S. patent application Ser. No. 09/543,214, entitled "Extravascular Hemodynamic Sensor", filed Apr. 5, 2000, which is incorporated herein by reference in its entirety. For example, multiple recesses can be included in housing 1206 for placement of the various optical elements. Alternatively, some or all of the optical elements can be placed in a header 1207 of device 1200. Placement in separate recesses guarantees that all detected light has interacted with the overlying tissue, and avoids the need for an optical barrier 1217 shown in FIGS. 12A–12C. In another embodiment, optical components are placed outside housing 1206 and connected to the internal circuitry via feed-through connector 1219. However, in contrast to the above described embodiment in which a recess is formed in the housing so that the external surface of the device remains flat, in the alternate embodiment no recess is provided. Rather, the device housing 1206 is left flat and the optical components are placed above it. An optical barrier prevents direct transmission of LEDs to the photodetector. In this embodiment, the optical components can be encased in an encapsulant, such as an epoxy, such that the components are mechanically stabilized and separated from the tissue. These are just a few example of how optical components can be positioned. In each of the above described exemplary embodiments, light source 302 and light detector 310 are incorporated into the housing of the implantable device. Further, LEDs 504a, 504b are arranged to transmit light having a first wavelength and light having a second wavelength in a direction generally away from the housing. Photodetector 512 can thereby detect light that has been reflected from tissue within the body of a patient within whom the device is implanted.

Further Embodiments

The above embodiments describe the use of two LEDs 504a, 504b and one photodetector 512. One of the LEDs transmits light at a wavelength less than 650 nm (e.g., 600 nm) and the other transmits light having a wavelength greater than 650 nm (e.g., 805 nm). The same photodetector is used to receive reflected and/or transmitted light having the first frequency and light having the second frequency. The use of time division multiplexing is used to distinguish between or separate the light at the different frequencies, as explained in detail above.

In an alternative embodiment, two LEDs and two photodetectors are used. One of the LEDs transmits light at the first wavelength and the other transmits light at a the second wavelength. One of the photodetectors is used to detect the light of the first wavelength, where the other is used to detect light of the second wavelength. Time division multiplexing can be used such that only one of the LEDs at a time is transmitting light and only the appropriate detector is detecting the transmitted light. Alternatively, optical filters (e.g., appropriate thin films) can be placed over the photodetectors so that the appropriate frequencies are detected at each photodetector. In the embodiment using optical filters, both LEDs can be transmitting light at the same time.

In still another embodiment, a broad spectrum source such as a tungsten halogen lamp or a incandescent lamp can be used to transmit light having a broad spectrum of wavelengths including the first and second wavelengths of interest. Two photodetectors are used, each covered by an appropriate optical filter, such that one of the photodetectors detects light having the first wavelength and the other photodetector detects light having the second wavelength.

In the embodiments that use two photodetectors, each photodetector can have its own associated signal conditioning circuitry. For example, referring back to FIG. 5, a current signal $i_{pd}$ produced by one of the photodetectors can drive its own current to voltage converter 514, with the output feeding its own filter 522. That is, the block diagram would look similar to that in FIG. 5, except there would be two separate current-to-voltage converters 514, and no need for demultiplexor 518 because there would be two distinct signal paths. Of course this is just one example of how to implement embodiments where there are two photodetectors.

The plethysmography signal (e.g., signal 316) produced using the present invention can be provided to an analog to digital (A/D) converter and then to a processor (e.g., a microprocessor) for analysis and/or for use in optimization algorithms or for any other purpose. A time domain analysis of the plethymography signal (e.g., after A/D conversion) can be used to calculate pulse amplitude. This can be accomplished by identifying a maximum amplitude, a minimum amplitude, and a difference between the two. An average value for pulse amplitude can also be determined. A frequency domain analysis can be used to calculate spectral power at, for example: the frequency of the heart rate, the frequency of respiration and/or at DC. These are just a few examples of how plethysmography signals produced using embodiments of the present invention can be processed.

All or some of the signal processing performed on the signals produced by photodetector 512 (or any other photodetector) can be performed in the digital domain, while still being within the spirit and scope of the present invention. For example, the signals produced by photodetector 512, or by current-to-voltage converter 514, can be immediately converted into the digital domain and all further processing of these signals (e.g., to determine the differences between detected intensities) can be determined in the digital domain, rather than using analog components. Such digital domain processing can be performed using dedicated digital hardware or on a general purpose processor, such as a microprocessor.

As mentioned above, plethysmography devices might be used, for example, in the cardiac department or intensive care department of a hospital or in a clinic for diagnostic purposes related to vascular surgery. There are numerous applications for which plethysmography signals produced using embodiment of the present invention can be used. Stated another way, there are various types of information one may want to derive from a plethysmography signal. These types of information include, for example, assessment of hemodynamic performance and respiration monitoring. Assessment of hemodynamic performance can include, but is not limited to: pacing parameter optimization (e.g., AV delay, RV-LV delay); optimization of pacing mode (e.g., VDD vs. DDD); arrhythmia discrimination/tailoring antiarrhythmic therapy; heart failure monitoring; assessment of autonomic tone; capture verification; and sensing optimization. Exemplary pacing parameter optimization algorithms are disclosed in U.S. patent application Ser. No. 09/759,395, entitled "Methods, Systems and Devices for Optimizing Cardiac Pacing Parameters", filed Jan. 12, 2001, and U.S. patent application Ser. No. 09/780,735, entitled "Methods, Systems and Devices for Optimizing Cardiac Pacing Parameters Using Evolutionary Algorithms", filed Feb. 9, 2001, each of which is assigned to the same assignee as the present invention, and each of which is incorporated herein by reference in its entirety. Respiration monitoring can include, but is not limited to: rate responsive pacing; heart failure monitoring (e.g., Cheynes-Stokes respiration, dypnea, hypopnea); sleep apnea monitoring (e.g., Cheynes-Stokes respiration, dypnea, hypopnea); and monitoring of pulmonary function (e.g., with asthma patients or chronic obstructive pulmonary disease patients).

The previous description of the preferred embodiments is provided to enable a person skilled in the art to make or use the present invention. While the invention has been particularly shown and described with reference to preferred embodiments thereof, it will be understood by those skilled in the art that various changes in form and details may be made therein without departing from the spirit and scope of the invention.

What is claimed is:

1. A method for reducing motion artifacts when monitoring volume changes in blood vessels, comprising the following steps:

(a) transmitting, from a light source implanted within a patient's body, light having a first wavelength and light having a second wavelength toward tissue within the patient's body;

(b) receiving a portion of the light having the first wavelength and a portion of the light having the second wavelength reflected from the tissue;

(c) producing a first signal, based on the received portion of light having the first wavelength, and a second signal, based on the received portion of light having the second wavelength;

(d) subtracting one of the first and second signals from the other to produce a plethysmography signal that is representative of volume changes in blood vessels of the tissue; and (e) setting intensities such that a ratio of an intensity of the light having the first wavelength over an intensity of the light having the second wavelength is approximately equal to a ratio of an effective absorption coefficient of non-blood tissue at the second wavelength over an effective absorption coefficient of non-blood tissue at the first wavelength.

2. The method of claim 1 wherein the setting intensities step comprises setting the intensities of the light transmitted at step (a).

3. A method for reducing motion artifacts when monitoring volume changes in blood vessels, comprising the following steps of:
   (a) transmitting light having a first wavelength and light having a second wavelength through a human appendage;
   (b) setting the transmitted intensity of at least one of the light having the first wavelength and the light having the second wavelength such that a ratio of an intensity of the light having the first wavelength over an intensity of the light having the second wavelength is approximately equal to a ratio of an effective absorption coefficient of non-blood tissue at the second wavelength over an effective absorption coefficient of non-blood tissue at the first wavelength;
   (c) receiving a portion of the light having the first wavelength and a portion of the light having the second wavelength;
   (d) producing a first signal, based on the received portion of light having the first wavelength, and a second signal, based on the received portion of light having the second wavelength; and
   (e) subtracting one of the first and second signals from the other to produce a plethysmography signal that is representative of volume changes in blood vessels of the human appendage.

4. The method of claim 3, wherein the setting intensities step comprises setting the intensities of the light transmitted at step (a).

5. A method for reducing motion artifacts when monitoring volume changes in blood vessels, comprising the following steps:
   (a) applying light having a first wavelength and light having a second wavelength to an epidermis of a patient;
   (b) detecting, at the epidermis of the patient, a portion of the light having the first wavelength and a portion of the light having the second wavelength;
   (c) producing a first signal, based on the detected portion of light having the first wavelength, and a second signal, based on the received portion of light having the second wavelength;
   (d) setting intensities such that a ratio of an intensity of the light having the first wavelength over an intensity of the light having the second wavelength is approximately equal to a ratio of an effective absorption coefficient of non-blood tissue at the second wavelength over an effective absorption coefficient of non-blood tissue at the first wavelength; and
   (e) subtracting one of the first and second signals from the other to produce a plethysmography signal that is representative of volume changes in blood vessels beneath the epidermis of the patient.

6. The method of claim 5, wherein the setting intensities step comprises setting the intensities of the light applied at step (a).

7. A method for reducing motion artifacts when monitoring volume changes in blood vessels, comprising the following steps of:
   (a) transmitting light having a first wavelength and light having a second wavelength through a human appendage;
   (b) receiving a portion of the light having the first wavelength and a portion of the light having the second wavelength;
   (c) producing a first signal, based on the received portion of light having the first wavelength, and a second signal, based on the received portion of light having the second wavelength;
   (d) adjusting a ratio of a gain of the first signal and a gain of the second signal to reduce motion artifacts; and
   (e) subtracting one of the first and second signals from the other to produce a plethysmography signal that is representative of volume changes in blood vessels of the human appendage.

8. The method of claim 7, wherein the ratio is adjusted to minimize the motion artifacts.

9. A method for reducing motion artifacts when monitoring volume changes in blood vessels, comprising the following steps:
   (a) applying light having a first wavelength and light having a second wavelength to an epidermis of a patient;
   (b) detecting, at the epidermis of the patient, a portion of the tight having the first wavelength and a portion of the light having the second wavelength;
   (c) producing a first signal, based on the detected portion of light having the first wavelength, and a second signal, based on the received portion of light having the second wavelength;
   (d) adjusting a ratio of a gain of the first signal and a gain of the second signal to reduce motion artifacts; and
   (e) subtracting one of the first and second signals from the other to produce a plethysmography signal that is representative of volume changes in blood vessels beneath the epidermis of the patient.

10. The method of claim 9, wherein the ratio is adjusted to minimize the motion artifacts.

* * * * *